US011332796B2

(12) United States Patent
Chiu

(10) Patent No.: US 11,332,796 B2
(45) Date of Patent: May 17, 2022

(54) COMPOSITION AND METHOD FOR CONCENTRATION AND ENRICHMENT OF NUCLEIC ACIDS

(71) Applicant: Phase Scientific International, Ltd., Hong Kong (CN)

(72) Inventor: Yin To Chiu, Hong Kong (CN)

(73) Assignee: Phase Scientific International, Ltd., Hong Kong (CN)

(*) Notice: Subject to any disclaimer, the term of this patent is extended or adjusted under 35 U.S.C. 154(b) by 0 days.

(21) Appl. No.: 16/961,245

(22) PCT Filed: Jan. 18, 2019

(86) PCT No.: PCT/US2019/014202
§ 371 (c)(1),
(2) Date: Jul. 9, 2020

(87) PCT Pub. No.: WO2019/143943
PCT Pub. Date: Jul. 25, 2019

(65) Prior Publication Data
US 2021/0079480 A1    Mar. 18, 2021

Related U.S. Application Data

(60) Provisional application No. 62/619,355, filed on Jan. 19, 2018.

(51) Int. Cl.
*C12Q 1/6886* (2018.01)
*C12N 15/10* (2006.01)

(52) U.S. Cl.
CPC ....... *C12Q 1/6886* (2013.01); *C12N 15/1006* (2013.01); *C12Q 2600/158* (2013.01)

(58) Field of Classification Search
CPC ............ C12Q 1/6886; C12Q 2600/158; C12N 15/1006; C12N 15/1003
See application file for complete search history.

(56) References Cited

U.S. PATENT DOCUMENTS

| | | | |
|---|---|---|---|
| 6,132,763 A | 10/2000 | Fisher | |
| 6,399,385 B1 | 6/2002 | Croyle et al. | |
| 7,626,017 B2 | 12/2009 | Laugharn, Jr. et al. | |
| 7,666,583 B2 | 2/2010 | Mor et al. | |
| 7,803,405 B2 | 9/2010 | Keating et al. | |
| 9,823,247 B2 | 11/2017 | Kamei et al. | |
| 10,006,911 B2 | 6/2018 | Kamei et al. | |
| 10,359,423 B2 | 7/2019 | Kamei et al. | |
| 10,578,616 B2 | 3/2020 | Kamei et al. | |
| 2002/0042506 A1 | 4/2002 | Kristyanne et al. | |
| 2005/0077497 A1 | 4/2005 | Anderson | |
| 2006/0025579 A1 | 2/2006 | Riedl et al. | |
| 2006/0166349 A1* | 7/2006 | Kepka ................ | C12N 15/1006 435/270 |
| 2008/0242825 A1 | 10/2008 | Devi et al. | |
| 2009/0192111 A1 | 7/2009 | Bader et al. | |
| 2009/0286966 A1 | 11/2009 | Christensen et al. | |
| 2010/0174052 A1* | 7/2010 | Hjorth ...................... | C07K 1/20 530/388.1 |
| 2010/0179252 A1* | 7/2010 | Johansson ............... | C08L 33/02 524/27 |
| 2011/0257378 A1* | 10/2011 | Tran ..................... | C07K 16/065 530/421 |
| 2011/0263040 A1 | 10/2011 | Jones | |
| 2013/0164825 A1 | 6/2013 | Christoffel et al. | |
| 2014/0221549 A1 | 8/2014 | Bodkhe et al. | |
| 2014/0227712 A1 | 8/2014 | Horlitz et al. | |
| 2014/0228549 A1 | 8/2014 | Burghoff et al. | |
| 2015/0253320 A1 | 9/2015 | Kamei et al. | |
| 2020/0284791 A1 | 9/2020 | Kamei et al. | |

FOREIGN PATENT DOCUMENTS

| | | |
|---|---|---|
| CN | 101679481 A | 3/2010 |
| CN | 102272144 A | 12/2011 |
| CN | 106662582 A | 5/2017 |
| CN | 110003323 A | 7/2019 |
| EP | 0268946 A2 | 6/1988 |
| WO | 0050161 A1 | 8/2000 |
| WO | 2011159537 A2 | 12/2011 |
| WO | 2015134938 A1 | 9/2015 |
| WO | 2016155888 A1 | 10/2016 |
| WO | 2017041030 A1 | 3/2017 |
| WO | 2018039139 A1 | 3/2018 |
| WO | 2018183454 A1 | 10/2018 |
| WO | 2018183465 A1 | 10/2018 |
| WO | 2018222972 A1 | 12/2018 |
| WO | 2019046553 A1 | 3/2019 |
| WO | 2019046563 A1 | 3/2019 |
| WO | 2019055926 A2 | 3/2019 |
| WO | 2019118712 A1 | 6/2019 |
| WO | 2019143895 A1 | 7/2019 |
| WO | 2019143943 A2 | 7/2019 |
| WO | 2019144016 A1 | 7/2019 |
| WO | 2019144030 A1 | 7/2019 |

OTHER PUBLICATIONS

Luechau, Frank; et al. (2009) Primary capture of high molecular weight nucleic acids using aqueous two-phase systems. Separation and purification technology, 66.1: 202-207.
Nazer, Behzad; et al. (2017) Plasmid DNA affinity partitioning using polyethylene glycol-sodium sulfate aqueous two-phase systems. Journal of Chromatography B, 1044: 112-119.
Sorber L, et al. (2017) A Comparison of Cell-Free DNA Isolation Kits: Isolation and Quantification of Cell-Free DNA in Plasma. J Mol Diagn. Jan;19(1):162-168.
Ziegler YS, et al. (2014) Plasma membrane proteomics of human breast cancer cell lines identifies potential targets for breast cancer diagnosis and treatment. PLoS One. 9(7):e102341.
Schindler J, et al. (2008) Aqueous polymer two-phase systems for the proteomic analysis of plasma membranes from minute brain samples. J Proteome Res 7(1):432-442.

(Continued)

*Primary Examiner* — Joseph G. Dauner
(74) *Attorney, Agent, or Firm* — Eagle IP Limited; Jacqueline C. Lui; Jennifer G. Che

(57) ABSTRACT

The present invention relates to a fast and efficient method of isolating nucleic acids in high yield and in high concentration from biological samples, using an aqueous two phase system without the need for instrumentation. The isolated nucleic acids can be used to facilitate the screening, prognosis and monitoring of disease progression.

14 Claims, No Drawings

(56) References Cited

OTHER PUBLICATIONS

Spindler KL, et al. (2015) Circulating free DNA as biomarker and source for mutation detection in metastatic colorectal cancer. PLoS One.10(4):e0108247.

Riedl W, et al. (2008) Membrane-supported extraction of biomolecules with aqueous two-phase systems[J]. Desalination, 224(1-3): 160-167.

Frerix A, et al. (2005) Scalable recovery of plasmid DNA based on aqueous two-phase separation. Biotechnol Appl Biochem. 42(Pt 1):57-66.

Crucho CIC, et al. (2017) Polymeric nanoparticles: A study on the preparation variables and characterization methods. Mater Sci Eng C Mater Biol Appl. 80:771-784.

Shin H, et al. (2015) High-yield isolation of extracellular vesicles using aqueous two-phase system. Sci Rep. 5:13103.

Zeringer E, et al. (2015) Strategies for isolation of exosomes. Cold Spring Harb Protoc. (4):319-323.

Iqbal M, et al. (2016) Aqueous two-phase system (ATPS): an overview and advances in its applications. Biol Proced Online. 18:18.

Zhou et al. (2015) Nanoparticle Vesicles with Controllable Surface Topographies through Block Copolymer-Mediated Self-Assembly of Silica Nanospheres, Langmuir, vol. 31(48), 11 pp. 13214-13220.

Bashir et al. (2016) Controlled-release of Bacillus thurigiensis formulations encapsulated in light-resistant colloidosomal microcapsules for the management of lepidopteran pests of Brassica crops, PEERJ., vol. 4(e2524). pp. 1-14.

Sigma-Aldrich "Poly(ethylene glycol) octyl ether" Retrieved from the Internet <URL:https://www.google.com/search?q=poly%28ethylene+glycol%29+octyl+ether&source=Int&tbs=cdr%3A1%2Ccd_min%3A%2Ccd_max%3A1%2F18%2F2018&tbm=> <URL https://www.sigmaaldrich.com/catalog/product/sigma/40530?lang=en&region=US> [retrieved on Jun. 16, 2020].

Frank Luechau, et al., Partition of plasmid DNA in polymer-salt aqueous two-phase systems, Separation and Purification Technology, Apr. 20, 2009, pp. 397-404, vol. 66, No. 2, Elsevier Science, Amsterdam, NL.

Vijayaragavan K. Saagar et al., Separation of porcine parvovirus from bovine serum albumin using PEG-salt aqueous two-phase system, Journal of Chromatography B, Sep. 1, 2014, pp. 118-126, vol. 967, NL.

Erik Jue et al., Using an aqueous two-phase polymer-salt system to rapidly concentrate viruses for improving the detection limit of the lateral-flow immunoassay: Concentrating Viruses in a Polymer-Salt System, Biotechnology and Bioengineering, Dec. 1, 2014, pp. 2499-2507, vol. 111, No. 12, US.

Paz Sean et al., A simplified SARS-CoV-2 detection protocol for research laboratories, PLOS ONE, Dec. 18, 2020, p. e0244271, vol. 15, No. 12.

* cited by examiner

COMPOSITION AND METHOD FOR CONCENTRATION AND ENRICHMENT OF NUCLEIC ACIDS

CROSS-REFERENCE TO RELATED APPLICATIONS

This application claims the benefit of U.S. Provisional Application No. 62/619,355, filed Jan. 19, 2018. The entire contents and disclosures of the preceding application are incorporated by reference into this application.

Throughout this application, various publications are cited. The disclosures of these publications in their entireties are hereby incorporated by reference into this application to more fully describe the state of the art to which this invention pertains.

FIELD OF THE INVENTION

The present invention relates to a composition, in particular to a composition comprising an aqueous biphasic system, more particularly to the aforesaid composition further comprising a phase separation promoter. The present invention also relates to the use of the aforementioned composition, in particular in the concentration of nucleic acids.

BACKGROUND OF THE INVENTION

The isolation and purification of nucleic acids is a critical first step in many research and diagnostic applications. Purified nucleic acids must be of high quality and reach sufficient quantity, such that they can be used in various downstream applications including detection, sequencing, and clinical diagnosis. Obtaining purified nucleic acids is a complicated task due to the presence of large amounts of contaminating cellular materials, (e.g. proteins and carbohydrates) present in the complex environments in which the nucleic acids are identified, including urine, blood, plasma, serum, saliva and other biological fluids.

In certain categories of target nucleic acids that are present at very low concentrations in biological fluids, such as urine and blood, there is a need to obtain large volumes of biological fluids in order to obtain sufficient quantity of nucleic acid for subsequent detection by molecular techniques.

There are a variety of methods that have been used for the purification of nucleic acids. These include precipitation, ultrafiltration (Hirasaki et al., J. Membr. Sci., 106: 123-129 (1995)) and also adsorption using anion-exchange columns. Other methods tested including commercially available methods are reported to have lower DNA extraction yields and to fail to extract small DNA fragments of less than 200 bp in length (Fong et al, Clinical Chemistry 55(3), 587-589, 2009).

There are several commercially available DNA extraction products (e.g. the QIAamp® Circulating Nucleic Acid Kit produced by Qiagen™) for extracting cell-free nucleic acids from blood, serum or plasma. Such extraction methods require the typical sample volumes in the range of 1-5 mL of biological fluids that may not be able to provide sufficient concentration of cell-free nucleic acids for the analysis.

As such, there remains a need for a faster and efficient processing method of nucleic acids using a concentration technique that requires shorter operating time and provides high yield of target nucleic acids, and at the same time handles large volumes of biological samples/fluids.

SUMMARY OF THE INVENTION

Accordingly, the present invention has been made to solve the problems occurring in the prior art, and an object of the present invention is to provide a novel composition comprising one or more phase separation promoters in aqueous biphasic system (ABS) (alternatively, aqueous two-phase system, ATPS) for the concentration and enrichment of nucleic acids, which facilitates a faster and efficient distribution of nucleic acids in an aqueous two-phase system without the need for complex instrumentation and allows for the purification of nucleic acids from large volume and complex biological materials with high yield, while avoiding nucleic acid contamination.

According to a first aspect of the present invention, there is provided a composition comprising:
1) an aqueous biphasic system comprising at least one polyether polymer, the polyether polymer containing at least 16 units of ethylene oxide (EO) moieties; and
2) one or more phase separation promoters.

In one embodiment, the polyether polymer contains a chain with at least 16 units of EO moieties. In one embodiment, the polyether polymer contains at least 16 units of EO moieties across more than one chains. In one embodiment, all EO moieties are linked together (e.g., $[-CH_2-CH_2-O-]_{16}$. In one embodiment, all or some of EO moieties are randomly or alternatingly distributed along a single chain or across different chains. In one embodiment, the electrolyte includes a substance that dissociates to ionic species when dissolved in water. The electrolyte may be selected from:
a) Simple ionic compounds, such as salts of phosphate, sulfate or citrate; and
b) Polyelectrolytes.

In one embodiment, the aqueous biphasic system, after phase separation, comprises two aqueous phases, i.e., one is a polymer phase (alternatively "polymer-rich phase") and the other is a salt phase (alternatively "salt-rich phase"). In one embodiment, the phase separation is due to electrostatic repulsion force among the components in the system. The salt phase or salt-rich phase refers to the phase in which the salt is predominantly distributed after phase separation. The polymer phase or polymer-rich phase refers to the phase in which the polymer is predominantly distributed after phase separation.

In some embodiments, it has been found that the present aqueous biphasic system (ABS) comprising polyether copolymers having at least 90 units of ethylene oxide (EO) moieties achieves advantageous concentration and enrichment of cell-free nucleic acids with a length below 300 base pairs. It has further been found that a composition comprising a polyether polymer having a chain of at least 16 ethylene oxide (EO) units and a hydrophobic portion, in which the ratio of the number of ethylene oxide (EO) units to the length of the hydrophobic portion of the polyether polymer is in a particular ratio achieves an advantageous concentration and enrichment of cell-free nucleic acid with a length below 300 base pairs. More particularly, the recovery of cell-free nucleic acids with a length below 300 base pairs is increased when the ratio of the number of ethylene oxide (EO) units to the length of the hydrophobic portion of the polyether polymer is bigger than 0.5. In one embodiment, the ratio is in the range of 0.5 to 3.0.

In this invention, the target nucleic acids are located in either the upper phase or lower phase, depending on the compositions of ABS which are known to the skilled person in the field. In one embodiment, aqueous biphasic system (or aqueous two phase system) refers to a system that is capable of separating into two phases, either spontaneously or with help of external force. In one embodiment, aqueous biphasic system (or aqueous two phase system) refers to a unstable composition or solution that is capable of separating into two phases. In one embodiment, the predominant partition of an analyte into one of the two phases is used for concentration, isolation or purification of the analyte.

In a further aspect, the present invention provides a composition comprising:
   a) at least one polyether polymer having a poly(ethylene oxide) chain of at least 16 ethylene oxide (EO) units and a hydrophobic portion, in which the ratio of the number of ethylene oxide (EO) units to the length of the hydrophobic portion of the polyether polymer is at least 0.5; and
   b) one or more phase separation promoters comprising an electrolyte or polyelectrolyte.

In a further aspect, the present invention provides a method of concentration and enrichment of cell-free nucleic acids with a length below 300 base pairs, comprising applying a composition as hereinbefore defined to a biological fluid or biological sample. In one embodiment, the biological sample can be a liquid, gel, solid, or any biological tissues that contains nucleic acids. In one embodiment, biological sample solution also means a solution generated by applying (or contacting) the aqueous biphasic system to (or with) the biological sample. In one embodiment, the in situ generated solution is directly used for subsequent isolation and/or analysis.

In one embodiment, there is provided a method of concentrating and enriching cell-free nucleic acids, comprising applying a composition as hereinbefore defined to a biological fluid.

It has been found that the compositions of the present invention achieve enhanced enrichment of cell-free nucleic acids from biological fluids, in particular the enrichment of cell-free nucleic acids with a size below 300 base pairs from biological fluids. Use of the present compositions in the concentration and enrichment of cell-free nucleic acids results in obtaining concentrated amount of nucleic acids from large volume of biological fluids containing trace amount of nucleic acids. As a result, the analysis of the concentrated cell-free nucleic acids can facilitate the screening, prognosis and monitoring of disease progression, in particular in the detection and monitoring of cancer. Further, the high concentration of cell-free nucleic acids obtained from biological fluids in a non-invasive way reduces potentially harmful effects to patients.

The present invention is very useful in the early diagnosis of tumor. It is believed that cell-free DNA (cfNDA) exists only in low levels (e.g., 30 ng/mL) in healthy individuals, but high levels (e.g., 180 ng/mL) of cell-free circulating tumor DNA (ctDNA) can be detected in cancer patients. In healthy individuals, the DNA fragments are usually 150-200 base pairs in length. By contrast, DNA released from cancer cells varies in the range of 100-600 base pairs. ctDNA is tumor-derived fragmented DNA in the blood and originates from a tumor. The analysis of ctDNA can provide the entire tumor genome information which is useful as a prognostic biomarker in diagnosis and monitoring of tumor progression in patients.

DETAILED DESCRIPTION OF THE INVENTION

The composition of the present invention is particularly useful in the concentration and enrichment of large volume of biological fluids, including blood, blood serum, blood plasma, gastric juice, salvia, urine, feces, tears and vomit that contain cell-free nucleic acids.

Nucleic acids subject to the present invention can be any nucleic acids; for examples, human nucleic acids, bacterial nucleic acids, or viral nucleic acids. In another embodiment, nucleic acids can be DNA, RNA, or DNA products of RNA obtained from reverse transcription or otherwise, single-stranded or double-stranded or in any other form. In some embodiments, the nucleic acids are cell-free nucleic acids, also referred to herein as circulating nucleic acids, not necessarily originating from a tumor.

Still further, the present invention provides a method of concentrating and enrichment of cell-free nucleic acids with a composition as hereinbefore described. The method of the invention can concentrate the cell-free nucleic acids in large quantities and volumes of biological fluids such as urine and blood, making the laboratory process simple and efficient.

As noted above, the composition of the present invention comprises a polyether polymer having a chain of ether-linked units comprising at least 16 units of ethylene oxide (EO) moieties.

Still further, the present invention provides at least a polyether polymer comprising a hydrophobic portion in combination with the chain of ethylene oxide (EO) units, in which the ratio of the number of ethylene oxide (EO) units to the length of the hydrophobic portion of the polyether polymer is at least 0.5. The polyether containing at least 16 units of ethylene oxide (EO) moieties can be prepared according to methods known in the art or methods analogous thereto. In one embodiment, the polyether polymers include fatty alcohol polyethylene glycol (AE09, Shree Vallabh Chemicals, reaction products of fatty acids with ethylene oxide (GPS, BASF), tristyryl polyether (Emulsogen® TS range, Clariant), tributylphenol polyether (Sapogenat® T range, Clariant), polyoxyethylene tristyrylphenol, polyoxyethylene-polyoxypropylene block copolymers, and octoxynol (Triton™ X). Many of the polyether polymers are commercially available.

In the composition of the present invention used in concentrating and enrichment of nucleic acids, the polyether polymer may be present in any suitable amount to provide a composition effective in concentrating and enrichment of nucleic acids. In one embodiment, the amount of the polyether polymer in the composition is in an amount of from 5 to 30% by weight. In one embodiment, the amount of the polyether polymer has an amount from 10 to 25%. In one embodiment, the amount of the polyether polymer has an amount of 15% to 20% by weight.

The polymers or copolymers of polyethers used in the composition may be branched, in particular hyperbranched. The term hyperbranching is a reference to polymer molecules having a high degree of branching. Hyperbranching of the polyether polymers may be obtained in known manner, for example, by crosslinking or grafting of groups such as hydroxyl, anionic or lipophilic groups. In one embodiment, the polymers or copolymers of polyethers used as separation promoters contain no or unsubstantially hyperbranching. In one embodiment, the polyether polymer also includes oligomer, and any molecules with molecular weight higher than 700 Da.

In the first aspect of the invention, the polyether polymer comprises a chain of ether-linked units comprising at least 16 ethylene oxide (EO) moieties. In one embodiment, the polyether polymer has at least 20 ethylene oxide (EO) moieties. In one embodiment, the polyether polymer has at least 25 ethylene oxide (EO) moieties. In one embodiment, the polyether polymer has 16 to 50 ethylene oxide (EO) moieties. In one embodiment, the polyether polymer has 18 to 45 EO moieties. In some embodiments of the invention, the polyether polymer comprises 20 to 40 EO moieties. In one embodiment, the polyether polymer has 20 to 35 EO moieties. In one embodiment, the polyether polymer has 25 to 35 EO moieties.

In one embodiment, the polyether polymers have at least 16 units of ethylene oxide (EO) moieties. In one embodiment, the polyether polymers include fatty alcohol polyethylene glycol, reaction products of fatty acids with ethylene oxide, tristyryl polyether, tributylphenol polyether, polyoxyethylene tristyrylphenol, polyoxyethylene-polyoxypropylene block copolymers, and octoxynol.

In a second aspect of the invention, the polyether polymer present in the composition comprises a hydrophobic portion in combination with a chain of ethylene oxide (EO) units, in which the ratio of the number of ethylene oxide (EO) units to the carbon number of the hydrophobic portion is at least 0.5. In one embodiment, the ratio is at least 1.0. In one embodiment, the ratio is at least 1.5. In one embodiment, the ratio is in a range of from 0.5 to 3.0. In one embodiment, the aforementioned ratio is in the range of from 0.7 to 2.5. In one embodiment, the ratio is in the range of from 1.0 to 2.0.

In one embodiment, the ratio of the number of ethylene oxide (EO) units to the length of the hydrophobic portion of the polyether polymer refers to the ratio of the EO units to the number of carbon atoms in the hydrophobic portion. For example, for a C16-C18 fatty alcohol polyglycol ether having 25 ethylene oxide units, the ratio is calculated as $25/16$ to $25/18$, which is 1.56 to 1.39.

In one embodiment, the "hydrophobic portion" refers to the hydrocarbon chain bonded to the ethylene oxide chain. Such hydrocarbon chains can be saturated or unsaturated, optionally substituted with alkyl groups. The length of the hydrophobic portion of the polyether polymer is based on the total number of carbon atoms of the hydrocarbon chain. For example, for an iso-tridecyl alcohol polyglycol ether with 16 ethylene oxide units, the ratio is $16/13$, that is 1.23. Furthermore, polyether polymers in the present invention include polyethers endcapped with an alkyl group. An example is $C_{12}$-$C_{18}$ fatty alcohol ethoxylate butyl ether with 16 EO units, which has a ratio of EO units to hydrophobic portion of 16/(12+4) to 16/(18+4), which is 1.00 to 0.80.

In one embodiment, the hydrophobic portion in the polyether polymers includes, but is not limited to, a fatty alcohol. In one embodiment, the polyether polymers include polyethers of fatty alcohols, for example, polyethers of oleyl alcohol and stearyl alcohol. In one embodiment, the polyether polymers are those derived from fatty acids, for example, lauric acid, myristic acid and coconut fatty acid. In one embodiment, the polyether polymers also include polyethers derived from block copolymers, such as polyoxyethylene-polyoxypropyiene block copolymers.

In one embodiment, the composition of the present invention comprises a polyether polymer having a chain of ether-linked units comprising at least 16 ethylene oxide (EO) moieties. In one embodiment, the polyether polymer further comprises a hydrophobic portion in combination with the chain of ethylene oxide (EO). In one embodiment, the ratio of the number of ethylene oxide (EO) units to the length of the hydrophobic portion of the polyether polymer is at least 0.5. In one embodiment, the ratio ranges from 0.5 to 3.0.

In yet a further aspect, the present invention provides the use of an electrolyte as a phase separation promotor. As described in more details hereinafter, the composition of the present invention may contain optionally one or more acceptable surfactants and/or one or more liquid carriers, depending upon the manner in which the composition is prepared.

In one embodiment, the present invention provides a composition and system for concentration and enrichment. In one embodiment, the weight percentage of the phase separation promoter in the composition may be adjusted to achieve the concentration and enrichment of nucleic acids with a length of less than 300 base pairs. In one embodiment, the weight percentage of the phase separation promoter is in the range of from 5% to 30%. In one embodiment, the weight percentage ranges from 10% to 25%. In one embodiment, the weight percentage ranges from 15% to 20%.

In one embodiment, the weight percentage of polyether polymer is in the range of from 5% to 30%. In one embodiment, the weight percentage ranges from 10% to 25%. In one embodiment, the weight percentage ranges from 15% to 20%.

In one embodiment, the electrolyte includes any substance that dissociates to ionic species when dissolved in water. In one embodiment, the electrolyte may be selected from:
 a) Simple ionic compounds, such as potassium phosphate and sodium chloride; and
 b) Polyelectrolytes.

In one embodiment, the simple ionic compound comprises a salt. In some embodiments, the salt can be selected from a magnesium salt, a lithium salt, a sodium salt, a potassium salt, a cesium salt, a zinc salt and an aluminum salt. In some embodiments, the salt is selected from a bromide salt, an iodide salt, a fluoride salt, a carbonate salt, a sulfate salt, a citrate salt, a carboxylate salt, a borate salt, and a phosphate salt. In some embodiments, the salt includes, but is not limited to, potassium phosphate, sodium phosphate, sodium chloride, sodium sulfate, magnesium sulfate, ammonium sulfate, sodium citrate, sodium acetate, ammonium chloride, potassium citrate, calcium phosphate, ammonium phosphate, ammonium citrate, ammonium acetate, magnesium phosphate, potassium sulfate, magnesium citrate, calcium sulfate, and any combinations thereof.

In some embodiments, the polyelectrolyte or the hydrophilic/water-soluble polymer includes but is not limited to polyethylene glycol, polypropylene glycol, cellulose ethers, chitosan, nylon resin, polyoxymethylene copolymer (U.S. 2016/0177091), polyvinyl alcohol, and combinations thereof. In one embodiment, a polyelectrolyte also comprises a hydrophilic/water-soluble polymer, such as polyacrylic acid, polystyrene sulfonate, or polyethylene glycol.

The composition of the present invention may contain optionally one or more auxiliaries. The auxiliaries employed depend upon such factors as the type of polymer and/or the length of the cell-free nucleic acids. Suitable auxiliaries include all customary adjuvants or components, such as solvents, surfactants, stabilizers, anti-foaming agents, anti-freezing agents, preservatives, antioxidants, colorants, thickeners and inert fillers. Such auxiliaries are known in the art and are commercially available.

The composition according to the present invention may further contain one or more surfactants. The number, type and amount of surfactant present will depend upon the nature of the formulation and the manner in which the composition is to be used. Suitable surfactants are known in the art and include, but are not limited to, Triton-X, Igepal CA-630, Nonidet P-40, and alkali metal.

The above compounds are listed as examples and are not intended to be an exhaustive list of compounds that can be used in the composition of the present invention.

The composition according to the present invention can be provided in any suitable forms, including but not limited to aqueous biphasic system. One skilled in the art will appreciate that the composition will vary. The composition may contain optionally one or more auxiliaries, and/or one or more surfactants. The exact composition can be adjusted or optimized depending on the actual need, or on the size of the nucleic acids.

The composition of the present invention further comprises a phase separation promoter, which is a compound that enhances or increases the phase separation in an aqueous biphasic system. In one embodiment, the phase separation promoters include but are not limited to electrolytes and polyelectrolytes. In one embodiment, the phase separation promoters do not include the polyether polymer. In one embodiment, the phase separation promoters include the polyether polymer that are modified as polyelectrolytes. In one embodiment, the phase separation promoters include but are not limited to modified polyether polymers that carry electrolyte groups such as carboxylic acid, sulfonate, phosphate, amine, and any combination thereof.

In one embodiment, the nucleic acids subject to the present invention have 300 or less base pairs (bp). In one embodiment, the nucleic acids have 40 bp to 280 bp. In one embodiment, the nucleic acids have more 100-250 bp. In one embodiment, the nucleic acids have 120-170 bp.

In one embodiment, the present invention provides a method and system to concentrate a sample with a large volume in a range of 1 mL-20 mL. In one embodiment, the present invention provides a method and system to concentrate an analyte by 100 to 200 folds. In one embodiment, the present invention provides a method and system to reduce input volume by 100 to 200 folds, for example, from 10 mL to 50 µL. In one embodiment, the present invention provides method and system to recover an analyte with a yield of 90% to 100%. In one embodiment, the analyte is cfDNA. In one embodiment, the present invention provides a method and system to provide sufficient quantity of analyte for subsequent analysis or diagnosis.

In one embodiment, the present invention provides a method and system to isolate and analyte an analyte with a concentration as low as 10 ng/mL. In one embodiment, the present invention provides a method and system to isolate and analyze an analyte with a concentration as low as 20 ng/mL.

In one embodiment, the analyte to be isolated is cfDNA, ctDNA or their fragments. In one embodiment, the DNA fragments have a length of 100-600 bp. In one embodiment, the DNA fragments have a length of 100-300 bp.

In one embodiment, the present invention provides a method and system of an aqueous two-phase system with a solid matrix. In one embodiment, the solid matrix is a porous solid matrix.

In the present invention, the two-phase system after phase separation comprises a salt phase containing at least one water soluble inorganic or organic salt and a polymer phase containing the polyether polymer having a chain of at least 16 units of ethylene oxide (EO) moieties, wherein the polyether polymer further comprises a hydrophobic portion. In one embodiment, the ratio of the number of ethylene oxide (EO) units to the carbon numbers of the hydrophobic portion of the polyether polymer is in a range from 0.5 to 3.0.

In the present invention, the two-phase system can be embedded in a solid matrix. The solid matrix can be, but are not limited to, any types of paper, polymer foams, cellulose foams, foams, rayon fabric, cotton fabric, fabric, wood, stones and carbon fibers. In one embodiment, the solid matrix is pre-treated with the polyether polymer, salt or phase separation promoters. In one embodiment, the pretreatment is a simple coating without covalent connection. In one embodiment, the treatment refers to a coating via covalent bond between the matrix and the polyether polymer, or phase separation promoter. In one embodiment, a full amount of the polyether polymer, salt or phase separation promoter is pre-loaded into the solid matrix. In one embodiment, a fraction amount is pre-loaded into the solid matrix.

In the present invention, the purified and concentrated target biological material or nucleic acid can be collected from the phase containing the polyether polymer. The concentration of the target biological material or nucleic acid can be increased by 10×, 100×, or even more in some embodiments.

In one embodiment, the nucleic acid on polyether polymer-treated porous paper is eluted out of the porous paper using appropriate elution buffers or deionized water. In one embodiment, the isolated phase containing nucleic acids is not eluted but is stored on the porous paper for future use. For instance, after the isolation of nucleic acids using the present invention, the porous paper containing the target nucleic acids is dried and stored. In one embodiment, nucleic acids retained on the porous paper can be directly eluted for further analysis or treatment. In one embodiment, nucleic acids retained on the porous paper can be first dried and subsequently eluted for further analysis or treatment. The selection of the elution buffer may depend on the contemplated use of the purified nucleic acids. Examples of suitable elution buffers includes, but are not limited to, Tris-EDTA (TE) buffer, aqua bidest and PCR buffer. In one embodiment, the purified nucleic acid on porous paper is eluted in a tube containing TE buffer (10 mM Tris.Cl, 1 mM EDTA solution with pH 7.5), and the purified nucleic acid is recovered in a relatively small volume, e.g., less than 100 µL, and can be used for various downstream applications including analyte detection, sensing, forensic, diagnostic or therapeutic applications, sequencing, amplification, and the like. It can be used in later nucleic acid based biochemical and diagnostic detection procedures, such as large scale genomic mapping, post DNA shearing, library construction, and for next generation sequencing platform.

In one embodiment, the purified nucleic acid on polyether polymer-modified porous paper can be eluted for further analysis, including PCR, RT-PCR, real-time PCR, and real-time RT-PCR. The nucleic acid can be eluted by means of an aqueous buffer. The selection of the buffer is determined by the contemplated use of the purified nucleic acid. Examples of suitable buffer are TE buffer, aqua bidest and PCR buffer. In one embodiment, TE buffer is used, and the purified nucleic acid on porous paper is eluted in a tube containing TE buffer (10 mM Tris.Cl, 1 mM EDTA solution at pH 7.5), and the purified nucleic acid is recovered in a relatively small volume, e.g., less than 100 µL.

In one embodiment, the present invention discloses a method of isolating nucleic acids from a biological sample solution using an aqueous biphasic system as described herein. In one embodiment, the method comprises:

a) providing a composition comprising a polyether polymer and one or more phase separation promoters, wherein the polyether polymer comprises a poly(ethylene oxide) chain with at least 16 ethylene oxide (EO) units and a hydrophobic portion; and b) mixing the biological sample solution with the composition to form the aqueous biphasic system comprising a polymer-rich phase and a salt-rich phase, wherein the nucleic acids are isolated in the polymer-rich phase.

In one embodiment, the poly(ethylene oxide) chain has no more than 50 EO units.

In one embodiment, one or more phase separation promoters include but are not limited to ionic compounds and polyelectrolytes.

In one embodiment, the ionic compounds include but are not limited to potassium phosphate, sodium phosphate, sodium chloride, sodium sulfate, magnesium sulfate, ammonium sulfate, sodium citrate, ammonium chloride, potassium citrates, calcium phosphate, ammonium phosphate, ammonium citrate, ammonium acetate, magnesium phosphate, potassium sulfate, magnesium citrate, calcium sulfate and any combinations thereof, and the polyelectrolytes are selected from polyacrylic acids, polystyrene sulfonates, polyethylene glycols, polypropylene glycols, cellulose ethers, chitosan, and nylon resins.

In one embodiment, the hydrophobic portion includes but is not limited to alkyl, polyethers of fatty alcohols, polyethers of lauric acid, myristic acid and coconut acid, fatty alcohol polyethylene glycol, tristyryl polyether, tributylphenol polyether, polyoxyethylene tristyrylphenol, polyoxyethylene-polyoxypropylene block copolymers, and octoxynol.

In one embodiment, the ratio of the number of EO units to the number of carbon atoms in the hydrophobic portion is in the range of 0.5-3.0.

In one embodiment, the ratio of the number of EO units to the number of carbon atoms in the hydrophobic portion is in the range of 1.0-2.0.

In one embodiment, the composition comprises 5-30 wt % of the polyether polymer. In one embodiment, the composition comprises 5-30 wt % of the polyether polymer in an aqueous solution or buffer. In one embodiment, the composition is in a form of solution or solid that is provided by an approach as disclosed in this application.

In one embodiment, the composition comprises 5-30 wt % of one or more phase separation promoters as described herein. In one embodiment, the composition comprises 5-30 wt % of the polyether polymer in an aqueous solution or buffer.

In one embodiment, the biological sample solution is prepared from urine, blood, plasma, serum or saliva.

In one embodiment, the nucleic acids include but are not limited to cell-free nucleic acids, DNA, RNA, DNA product obtained from reverse transcription of RNA, and RNA product obtained from transcription of DNA.

In one embodiment, the nucleic acids have no more than 300 base pairs.

In one embodiment, the concentration of the nucleic acids in the polymer-rich phase is 100 to 200 times higher than that in the biological sample solution.

In one embodiment, the method isolates 90-100% of the nucleic acids from the biological sample solution.

In one embodiment of the present method, the step a) includes a step of applying the composition to a solid porous matrix.

In one embodiment, the solid porous matrix includes but is not limited to paper, polymer foams, cellulose foams, foams, rayon fabric, cotton fabric, fabric, wood, stones and carbon fibers.

In one embodiment, the present invention discloses a method for detecting or monitoring a disease in a subject, the method comprises:

a) preparing a solution of a biological sample containing target nucleic acids, wherein the biological sample is obtained from the subject;

b) isolating the target nucleic acids from the solution using the isolation method as disclosed in this invention;

c) obtaining sequence information of the target nucleic acids; and d) optionally determining the quantity of the target nucleic acids in the biological sample.

In one embodiment, the sequence information and the quantity of the target nucleic acids are indicative respectively of the presence and/or severity of the disease, thereby allowing detection and monitoring of the disease in the subject. In one embodiment, the sequence information and the quantity of the target nucleic acids are indicative combinedly of the presence and severity of the disease, thereby allowing detection and monitoring of the disease in the subject.

In one embodiment, the disease is cancer.

The present invention will be described in more detail with reference to the following examples. However, the following examples are provided only for assisting in the entire understanding of the present invention, and do not intend to limit the scope of the present invention. One skilled in the art will readily appreciate that the examples provided are merely for illustrative purposes and are not meant to limit the scope of the invention which is defined by the claims following thereafter.

Herein, unless indicated otherwise, the terms used in the specification including technical and scientific terms have the same meaning as those that are usually understood by those skilled in the art to which the present invention pertains, and detailed description of the known functions and constitutions that may obscure the gist of the present invention will be omitted.

Throughout this application, it is to be noted that the transitional term "comprising", which is synonymous with "including", "containing" or "characterized by", is inclusive or open-ended, and does not exclude additional, un-recited elements or method steps.

EXAMPLES

Determination of Phase Separation

The phase separation of aqueous biphasic system treated with the composition may be determined by the following procedure.

The compositions were prepared according to the example stated below. The phase separation was determined by the visual observation during the phase separation.

Example 1: Composition with 25% Polyether Polymer

An aqueous solution with the following composition (expressed in wt %) was prepared.

| | |
|---|---|
| $C_{16}$-$C_{18}$ fatty alcohol polyoxyethylene ether (25 EO) | 25% |
| Potassium phosphate ($K_3PO_4$) | 7.5% |
| Triton-X | 10% |

The phase separation of the solution was tested using the above testing method. The time for the phase separation is 11 min. By comparison, the time for phase separation obtained with the same composition but without the phase separation promoter, Potassium phosphate, was 21 min.

Example 2: Composition with 20% Polyether Polymer

An aqueous solution with the following composition (expressed in wt %) was prepared.

| | |
|---|---|
| Tristyryl polyoxyethylene ether (20 EO) | 20% |
| Dextran 70 | 10% |
| Triton-X | 15% |

The phase separation of the solution was tested using the above testing method. The time for the phase separation is 10 min. By comparison, the time for phase separation obtained with the same composition but without the phase separation promoter-polyoxymethylene was 20 min.

Example 3: Composition with 5% Polyether Polymer

An aqueous solution with the following composition (expressed in wt %) was prepared.

| | |
|---|---|
| Tributylphenol ethoxylate (25 EO) | 5% |
| Sodium phosphate | 5% |
| Triton-X | 10% |

The phase separation of the solution was tested using the above testing method. The time for the phase separation is 5 min. By comparison, the time for phase separation obtained with the same composition but without the phase separation promoter, sodium phosphate, was 20 min.

Determination of Yield of the Purified Nucleic Acids

The yield of the nucleic acids purified using the solution prepared in Examples 1 to 3 was tested as follows.

A volume of 4 mL of plasma was used for the Qiagen™ protocol, which requires the typical sample volumes in the range of 1-5 mL. This volume range may not be able to provide sufficient quantity of cell-free nucleic acids for analysis. However, a volume of 10 mL of plasma was used for the present invention which can handle larger volume of samples (e.g. 10 mL), so that a higher concentration fold can be achieved to provide sufficient quantity of analyte. The yields of double-stranded cfDNA recovered by the Qiagen™ method and the present method were determined. The final volume of cfDNA by these two methods were kept the same at 50 μL. Qubit fluorometer was used for the measurements of cfDNA recovery. It was found that the present invention achieved a 200-fold concentration by reducing input volume from 10 mL to 50 μL, much higher than the 80-fold achieved by the Qiagen™ method. In addition, the final yield of the present method is 100% while that of the Qiagen™ method is only 83%. Together with the advantage of handling large volume of samples (e.g. 10 mL), the present invention offers higher yield and performance of cfDNA concentration than the Qiagen™ protocol.

TABLE 1 cfDNA recovered after purification by the present method and Qiagen method

| Method | cfDNA recovered (ng) | Yield (%) | Concentration Fold |
|---|---|---|---|
| Qiagen method | 100 | 83% | 80 |
| Present invention | 300 | 100% | 200 |

What is claimed is:

1. A method of isolating nucleic acids from a biological sample solution using an aqueous biphasic system, comprising:
   a) providing a composition comprising a polyether polymer and one or more phase separation promoters, wherein said polyether polymer comprises a poly(ethylene oxide) chain with at least 16 ethylene oxide (EO) units and a hydrophobic portion; and
   b) mixing said biological sample solution with said composition to form said aqueous biphasic system comprising a polymer-rich phase and a salt-rich phase, wherein said nucleic acids are isolated in said polymer-rich phase,
   wherein said nucleic acids have no more than 300 base pairs;
   wherein said one or more phase separation promoters are selected from the group consisting of ionic compounds, polyelectrolytes and hydrophilic polymers; and
   wherein the ratio of the number of EO units to the number of carbon atoms in said hydrophobic portion is at least 0.5.

2. The method of claim 1, wherein said poly(ethylene oxide) chain has no more than 50 EO units.

3. The method of claim 1, wherein said ionic compounds are selected from the group consisting of potassium phosphate, sodium phosphate, sodium chloride, sodium sulfate, magnesium sulfate, ammonium sulfate, sodium citrate, ammonium chloride, potassium citrates, calcium phosphate, ammonium phosphate, ammonium citrate, ammonium acetate, magnesium phosphate, potassium sulfate, magnesium citrate, calcium sulfate and any combinations thereof, and said polyelectrolytes are selected from the group consisting of polyacrylic acid, polystyrene sulfonate, and said hydrophilic polymers are selected from the group consisting of polyethylene glycol, polypropylene glycol, cellulose ethers, chitosan, and nylon resin.

4. The method of claim 1, wherein said hydrophobic portion is selected from the group consisting of alkyl, polyethers of fatty alcohols, polyethers of lauric acid, myristic acid and coconut acid, fatty alcohol polyethylene glycol, tristyryl polyether, tributylphenol polyether, polyoxyethylene tristyrylphenol, polyoxypropylene, and octoxynol.

5. The method of claim 1, wherein the ratio of the number of EO units to the number of carbon atoms in said hydrophobic portion is in the range of 0.5-3.0.

6. The method of claim 1, wherein the ratio of the number of EO units to the number of carbon atoms in said hydrophobic portion is in the range of 1.0-2.0.

7. The method of claim 1, wherein the composition comprises 5-30 wt % of said polyether polymer.

8. The method of claim 1, wherein the composition comprises 5-30 wt % of said one or more phase separation promoters.

9. The method of claim 1, wherein said biological sample solution is prepared from urine, blood, plasma, serum or saliva.

10. The method of claim 1, wherein said nucleic acids are selected from the group consisting of cell-free nucleic acids, DNA, RNA, DNA product obtained from reverse transcription of RNA, and RNA product obtained from transcription of DNA.

11. The method of claim 1, wherein step a) includes a step of applying said composition to a solid porous matrix.

12. The method of claim 11, wherein said solid porous matrix is selected from the group consisting of paper, polymer foams, cellulose foams, foams, rayon fabric, cotton fabric, fabric, wood, stones and carbon fibers.

13. A method for detecting or monitoring a disease in a subject, comprising:
   a) preparing a solution of a biological sample containing target nucleic acids, said biological sample obtained from said subject;
   b) isolating said target nucleic acids from said solution using the method of claim 1;
   c) obtaining sequence information of the target nucleic acids; and
   d) optionally determining the quantity of said target nucleic acids in said biological sample;
   wherein said sequence information and said quantity of said target nucleic acids are indicative of the presence or severity of said disease, thereby allowing detection and monitoring of said disease in said subject.

14. The method of claim 13, wherein the disease is cancer.

\* \* \* \* \*